US005912000A

United States Patent [19]
Podolski et al.

[11] Patent Number: 5,912,000
[45] Date of Patent: Jun. 15, 1999

[54] CHITOSAN INDUCED IMMUNOPOTENTIATION

[75] Inventors: Joseph S. Podolski; Kuang Hsu, both of The Woodlands; Gurpreet Singh, Houston, all of Tex.

[73] Assignee: Zonagen, Inc., The Woodlands, Tex.

[21] Appl. No.: 08/696,170

[22] Filed: Aug. 13, 1996

Related U.S. Application Data

[63] Continuation of application No. 08/533,064, Sep. 26, 1995, abandoned, which is a continuation-in-part of application No. 08/311,532, Sep. 23, 1994, abandoned.

[51] Int. Cl.$^6$ ............... A61K 45/00; A61K 31/73; C07H 1/00
[52] U.S. Cl. ............... 424/278.1; 514/55; 536/123.1
[58] Field of Search ............... 424/278.1; 514/55; 536/123.1

[56] References Cited

U.S. PATENT DOCUMENTS

| | | | |
|---|---|---|---|
| 4,372,883 | 2/1983 | Matuhashi et al. | 436/543 |
| 4,713,249 | 12/1987 | Schröder | 424/488 |
| 4,810,695 | 3/1989 | Conti et al. | 514/55 |
| 4,814,169 | 3/1989 | Mitsuhashi et al. | |
| 4,877,612 | 10/1989 | Berger et al. | 424/92 |
| 4,895,724 | 1/1990 | Cardinal et al. | 424/418 |
| 4,935,147 | 6/1990 | Ullman et al. | 210/695 |
| 4,939,239 | 7/1990 | Matsuhashi et al. | 530/370 |
| 4,971,956 | 11/1990 | Suzuki et al. | 514/55 |
| 5,508,185 | 4/1996 | Kawamura et al. | 435/178 |

FOREIGN PATENT DOCUMENTS

| | | |
|---|---|---|
| 0 183 556 A2 | 6/1986 | European Pat. Off. |
| 0 308 147 A1 | 3/1989 | European Pat. Off. |
| 0 454 898 A1 | 11/1991 | European Pat. Off. |
| 62-061927 | 3/1987 | Japan |
| 4-0311385 | 11/1992 | Japan |
| 5-294846 | 11/1993 | Japan ............... A61K 39/39 |
| WO 84/00294 A1 | 2/1984 | WIPO |
| WO 96/10421 A1 | 4/1996 | WIPO |

OTHER PUBLICATIONS

Onsoyen, E. et al. "Metal recovery using chitosan." J. Chem. Technol. Biotechnol. (England), vol. 49, pp. 395–404 (Abstract only cited), 1990.
Edelman, "Vaccine Adjuvants," Rev.Infect.Dis. 2:370–383 (1980).
Freund et al., "Sensitization and Antibody Formation after Injection of Tubercle Bacilli and Paraffin Oil," Proc.Soc.Biol.Med. 37:509–513 (1937).
Gajewski et al., "Murine Th1 and Th2 Clones Proliferate Optimally in Response to Distinct Antigen–Presenting Cell Populations[1]," J.Immunol., 146:1750–1758 (1991).
Gajewski et al., "Antiproliferative Effect of IFN–γ in Immune Regulation," J.Immunol., 143:15–22 (1989).
Gery et al., "Stimulation of B–Lymphocytes by Endotoxin," J.Immunol., 108:1088–1091 (1972).
Grun et al., "Different T Helper Cell Subsets Elicited in Mice Utilizing Two Different Adjuvant Vehicles: The Role of Endogenous Interleukin 1 in Proliferative Responses," Cell.Immunol., 121:134–145 (1989).
Gupta et al., "Adjuvants—a balance between toxicity and adjuvanticity," Vaccine, 11:291–306 (1993).
Johnson et al., "Studies on the O Antigen of Salmonella Typhosa," J.Exp.Med., 103:225–246 (1956).
Marcinkiewicz et al., "Immunoadjuvant Properties of Chitosan," Arch.Immunol.Ther.Exp. 39:127–132 (1991).
Mosman and Coffman, "TH1 and TH2 Cells: Different Patterns Lymphokine Secretion Lead to Different Functional Properties," Ann.Rev.Immunol. 7:145–173 (1989).
Nishimura et al., "Effect of multiporous microspheres derived from chitin and partially deacetylated chitin on the activation of mouse peritoneal macrophages," Vaccine 5:136–140 (1987).
Nishimura et al., "Immunological Activity of Chitin and its Derivatives," Vaccine 2:93–99 (1984).
Ohta et al., "Adjuvant Action of Bacterial Lipopolysaccharide in Induction of Delayed–Type Hypersensitivity to Protein Antigens. II. Relationships of Intensity of the Action to that of Other Immunological Activities," Immunobiology 53:827 (1984).
Ramanathan et al., "Complement activation by aluminum and zirconium compounds," 37:881–888 (1979).
Siskind, "Manipulation of the Immune Response," Pharm. Rev. 25:319–324 (1979).
Tomai et al., "T Cell and Interferon–γ Involvement in the Adjuvant Action of a Detoxified Endotoxin," J.Biol.Resp.Med. 8:625–643 (1989).
Warren et al., "Current Status of Immunological Adjuvants," Ann.Rev.Immunol. 4:369–388 (1986).
White et al., "Studies on Antibody Production," J.Exp.Med. 102:73–82 (1955).
Audibert and Lise, "Adjuvants: Current Status, Clinical Perspectives and Future Prospects," TiPS, 14:174–178 (May, 1993).
Nishimura et al., "Macrophage Activation With Multi–Porous Beads Prepared Form Partially Deacetylated Chitin," J. Biomed. Mat. Res., 20:1359–1372 (1986).
Reid, G., "Soluble Proteins Incorporate into ISCOMs After Covalent Attachment of Fatty Acid," Vaccine, 10(9):597–602 (1992).
Leuthardt and Roesel, "Cloning, expression and purification of a recombinant poly–histidine–linked HIV-1 protease," FEBS Letters, 326(1,2,3):275–280 (Jul., 1993).
Kashkin, K.P. et al., "Some Properties of Chitosan as a Carrier in Conjugated Antigens," Immunologiya (Moscow), 2:31–35 (1984).
Tokura, S. et al., "Immunological Aspects of Chitin Derivatives," Industrial Polysaccharides: Genetic Engineering Structure/Property Relations and Applications, edited by M. Yalpani, Elsevier Science Publishers B.V., Amsterdam, Netherlands, pp. 347–362 (1987).

Primary Examiner—Michael P. Woodward
Attorney, Agent, or Firm—Marshall, O'Toole, Gerstein, Murray & Borun

[57] ABSTRACT

Methods and compositions for potentiating an immune response are disclosed which incorporate chitosan as an immunopotentiating adjuvant. Administration of the compositions of the invention is effected by various routes.

66 Claims, No Drawings

CHITOSAN INDUCED IMMUNOPOTENTIATION

This application is a continuation of to U.S. patent application Ser. No. 08/533,064 filed Sep. 26, 1995, now abandoned, which is a continuation-in-part of U.S. patent application Ser. No. 08/311,532, filed Sep. 23, 1994, now abandoned.

FIELD OF THE INVENTION

The present invention relates generally to methods for potentiating an immune response in an animal, compositions to effect the potentiation, and methods to produce the compositions. More specifically, the invention provides methods comprising the use of a protein/chitosan conjugate or a protein/chitosan suspension to potentiate an immune response, protein/chitosan conjugates or protein/chitosan suspensions to effect potentiation, and methods to prepare the protein/chitosan conjugate or protein/chitosan suspension.

BACKGROUND OF THE INVENTION

Recent biotechnological advances have facilitated identification of components in complex antigens which provide hope for successful development of safe and practical vaccines. Often, however, these isolated select components are not as immunogenic as the complete complex antigens from which they were derived. In order to enhance an immune response to the weakly antigenic immunogen in a recipient animal, adjuvants are frequently administered with the immunogen. Despite the universal acceptance of adjuvants, however, the number suitable for use in humans is limited.

Ideally, an adjuvant should potentiate long-lasting expression of functionally active antibodies, elicit cell-mediated immunity (CMI), and enhance production of memory T- and B-lymphocytes with highly specific immunoreactivity against an invading antigen. In addition to providing a defense upon immediate challenge with an foreign antigen, these responses should provide protection against any future encounters of the host with a specific antigen. More important is the ability of an adjuvant to augment the immune response with a minimum of toxic side effects. Therefore, efficacy of an adjuvant is described in terms of how it balances positive (potentiated immunity) and negative (toxicity) influences.

Controlled immunization for the purpose of stimulating antibody production by B cells is dependent upon a myriad of factors inherent to both the antigen itself and the immunized animal. In general, the farther removed in evolutionary terms the antigen, or its source, is from the invaded host, the more effective the immune response elicited by the antigen. Antigens derived from closely related species are less competent in eliciting antibody production due to the fact that the host immune system is unable to clearly distinguish the foreign antigen from endogenous, or self antigens. In addition, the dosage of the antigen, the purity of the antigen, and the frequency with which the antigen is administered are also factors which significantly contribute to the resulting antibody titer and specificity of the resulting antibodies. Still other factors include the form, or complexity, of the antigen, and how the antigen is administered. Finally, both the genetic makeup and overall physiological state of the immunized animal contribute to the extent to which an immune response is mounted. Of these factors, the form or complexity of the antigen is directly affected by immunization with an adjuvant.

Current understanding suggests that adjuvants act to augment the immune response by a variety of different mechanisms. In one mechanism, the adjuvant directly stimulates one of either CD4$^+$ helper T-cell subpopulations designated $T_H1$ or $T_H2$ [Mosmann and Coffman, Ann.Rev.Immunol. 7:145–173 (1989)]. Helper T cells are required for B-cell antibody responses to most antigens. In an appropriate immune response, an antigen is captured and processed by an antigen-presenting cell (APC), e.g., circulating or tissue macrophages, and presented on the surface of the APC in association with a class II major histocompatibility (MHC) molecule. In this form, the antigen can interact with receptors on the surface of helper T cells thereby activating the particular subpopulation of cells to express and secrete any of a number of cytokines. The nature of cytokine production depends on the subset of helper T cells activated, a result that can be modulated in part by the choice of adjuvant. For example, alum, an aluminum salt adjuvant approved for clinical use in humans, has been reported to selectively activate $T_H2$ cells in mice [Grun and Maurer, Cell.Immunol. 121:134–145 (1989)], while Freund's complete adjuvant FCA), an emulsion of mineral oil with killed mycobacteria [Freund, et al., Proc.Soc.Exp.Biol.Med. 37:509 (1937)], preferentially activates murine $T_H1$ cells [Grun and Maurer, Cell.Immunol. 121:134–145 (1989)].

Another mechanism by which the immune response is augmented involves the direct stimulation of B cells by, for example, lipopolysaccharide (LPS) from Gram-negative bacteria. [Gery, et al., J.Immunol. 108:1088 (1972)]. LPS has also been shown to stimulate secretion of interferon-γ (INF-γ) [Tomai and Johnson, J.Biol.Resp.Med. 8:625–643 (1989)], which both inhibits proliferation of $T_H2$ cells and stimulates differentiation of $T_H1$ cells [Gajewski, et al., J.Immunol. 143:15–22 (1989); Gajewski, et al., J.Immunol. 146:1750–1758 (1991)]. The mechanism by which LPS potentiates the immune response is therefore through direct stimulation of B cells, and indirect regulation of both $T_H1$ and $T_H2$ cell populations.

Still other modes of immunopotentiation have been reported for other adjuvants. Oil emulsions (i.e., Freund's complete adjuvant [FCA], Freund's incomplete adjuvant [FIA]) and liposomes act through depot formation as does alum, thus allowing for slow release of antigen. Slow release of antigen permits extended exposure of the antigen to the immune system and also allows for initial immunization with a dosage of antigen that, if delivered at one time, would ordinarily be counterproductive to antibody formation. It has been previously reported that while a large initial dose of antigen results in the production of a higher immediate titer of antibody, the increase in antibody titer and increase in antibody specificity as a function of time is not as great as observed with lower and more frequent doses of antigen [Siskind, G., Pharm.Rev. 25:319–324 (1973)]. Therefore, adjuvants which control presentation of an antigen to the immune system modulate antigen dosage in addition to altering the form, or complexity, of the antigen.

To date, only one adjuvant, alum [$AlK(SO_4)_2 \cdot H_2O$], has proven sufficiently non-toxic to permit its use in humans. Alum not only acts through $T_H2$ cell activation, depot formation and slow release of antigen following immunization [Edelman, Rev.Infect.Dis. 2:370–383 (1980); Warren, et al., Ann.Rev.Immunol. 4:369–388 (1986)], but also through granuloma formation by attracting immunocompetent cells [White, et al., J.Exp.Med. 102:73–82 (1955)] and activation of complement [Ramanathan, et al., Immunol. 37:881–888 (1979)]. However, alum is not without its negative side effects which include erythema, subcutaneous nodules, contact hypersensitivity, and granulomatous inflammation. Other adjuvants, which are widely employed outside of human application, are also the focus of continuing research to develop acceptable alternatives for use in humans. Included are the above mentioned oil emulsions (i.e., FCA and FIA), bacterial products (i.e., LPS, cholera toxin, mycobacterial components and whole killed *Corynebacterium parvum, Corynebacterium granulosum,* and *Bordetella pertussis,* liposomes, immunostimulating complexes (ISCOMs), and naturally occurring and derivatized polysaccharides from other than bacterial sources.

The immunopotentiating capacity of polysaccharides has been a focus of investigation over the past few years as these compounds are widespread in nature, e.g., as structural components in the cell walls of bacteria, and exoskeletons of insects and crustacea. Lipopolysaccharide (LPS) isolated from certain Gram-negative bacteria is one such polysaccharide even though the adjuvant properties of LPS are derived mainly from the lipid A region of the molecule, and not from the o-specific polysaccharide or core oligosaccharide regions of the molecule. LPS, which augments both humoral [Johnson, et al., *J.Exp.Med.* 103:225–246 (1956)] and cell-mediated immunity [Ohta, et al., *Immunobiology* 163:460–469 (1982)], possesses numerous biological activities, but is impractical for use in humans due to its inherent toxicity as reviewed by Gupta, et al., *Vaccine* 11:291–306 (1993). Attention has therefore shifted to other polysaccharides including, among others, chitosan.

Chitosan [β-(1-4)-2-amino-2-deoxy-D-glucan] is a derivative of chitin and has been widely used in biomedical applications, due in part to is biodegradability by lysozyme and low toxicity in humans. These same properties have resulted in increased interest in chitosan as an immunopotentiating agent. For example, Matuhashi, et al., in U.S. Pat. No. 4,372,883, disclosed conjugation of soluble polysaccharides, including chitosan, to normally toxic antigens, conjugation thereby detoxifying the antigen and permitting its use as an immunogen. Matuhashi et al., however, did not address the use of insoluble forms of chitosan, nor did Matuhashi compare the resulting serum antibody titer with that obtained from immunization with other known adjuvants.

Likewise, Suzuki, et al., in U.S. Pat. No. 4,971,956, disclosed the use of water soluble chitosan-oligomers as therapeutics for treatment of bacterial and fungal infections, as well as for the treatment of tumors. Suzuki, et al, discussed the difficulty in modifying chitosan to produce an appropriate water soluble form, disclosing that water-insoluble forms are impractical for therapeutic application. In addition, Suzuki et al., does not disclose conjugation of an antigen to chitosan to effect enhanced immune response.

Mitsuhashi, et al., in U.S. Pat. No. 4,814,169, disclosed the use of human protein conjugated to soluble polysaccharides, including chitosan, to generate antibodies against human protein in non-human animals. Administration of the human protein/polysaccharide solution was by intravenous, intraperitoneal, or subcutaneous injection. Other routes, including oral and rectal administration, were not addressed in the disclosure.

Nishimura, et al. [*Vaccine* 2:93–99 (1984)] reported the immunological properties of derivatives of chitin in terms of activation of peritoneal macrophages in vivo, suppression of tumor growth in mice, and protection against bacterial infection. Results suggested that both chitin and chitosan were ineffective stimulators of host resistance against challenge with tumor cells or bacteria, but that chitosan moderately induced cytotoxic macrophages. Results with modified, de-acetylated chitosan, which forms a gel in an aqueous environment, was shown to more effectively activate macrophages, suppress tumor growth and stimulate resistance to bacterial infection.

Marcinkiewicz, et al., [*Arch.Immunol. Ther.Exp.* 39:127–132 (1991)] examined the immunoadjuvant activity of water-insoluble chitosan and reported significant enhancement of T-dependent humoral response, but only moderate augmentation of T-independent humoral response. The enhanced humoral response was detected with chitosan at doses of 100 mg/kg administered either intravenously or intraperitoneaUy. Subcutaneous and oral administration were specifically reported as being ineffective. In addition, Marcinkiewicz, et al., does not suggest conjugation of an antigen to insoluble chitosan, stating that chitosan "resulted in the same response irrespective of the site of administration—either together or separately from antigen."

In light of the fact that only one existing adjuvant has been approved for use in humans, there thus exists a need in the art to provide novel and less toxic adjuvants for potential application in humans. Improved adjuvants will permit the production of more effective vaccines and will improve the production of monoclonal antibodies with therapeutic potential.

SUMMARY OF THE INVENTION

In one aspect, the present invention provides a method for potentiating an immune response comprising the steps of conjugating an antigen to a chitosan adjuvant and administering the protein/chitosan conjugate to an animal. The immune response is characterized by a rapid class switch from IgM to IgG production. The present invention encompasses antigens including antigens in the form of proteins, carbohydrates, lipids, glycoproteins or combinations thereof. The chitosan adjuvant may be soluble or insoluble; the insoluble adjuvant being either gelatinous or particulate in form. Conjugation of the antigen may be effected through chemical crosslinking, ionic interaction, physical intercalation, hydrophobic interactions, hydrophilic interactions, or covalent modification. A preferred method for crosslinling an antigen to the adjuvant is via use of glutaraldehyde. When glutaraldehyde is used for crosslinking, the resulting antigen/chitosan immunogen may be either particulate or gelatinous, depending on the degree of crosslinking. The ratio of antigen to chitosan may range from 1:100 to 100:1, but is preferable in the range of 1:4 to 1:10, all ratios being weight of antigen to wet weight of chitosan. An alternative preferred ratio is 10:1. Antigen may be conjugated to the particulate chitosan adjuvant on the exterior surface of the particle, on an interior surface of the particle, or a combination of both interior and exterior conjugation. The antigen/chitosan conjugate may be administered to the animal orally, intra-nasally, intra-vaginally, intra-rectally, or via intraperitoneal, intravenous, or subcutaneous injection; administration may comprise a single route or a multiplicity of routes. The antigen/chitosan conjugate may be administered alone, or in combination with any of a number of other adjuvants. Immunization may comprise a single administration or a multiplicity of administrations.

In another aspect, the invention provides an adjuvant comprising, in combination, chitosan with a chelated metal ion. The metal ion may, for example be iron or a transition metal such as copper, nickel, or zinc.

Also provided in an immunogen, the immunogen comprising chitosan with a chelated metal ion and an antigen.

The antigen can include, but is not limited to proteins, carbohydrates, lipids, glycoproteins or combinations thereof. Protein antigens may be naturally occurring or recombinant. The antigen may be conjugated to the adjuvant by covalent bonding. Preferred covalent attachment is via crosslinking using glutaraldehyde. The resulting crosslinked immunogen may be particulate or gelatinous, depending on the degree of crosslinking. The antigen may also be combined with the adjuvant through ionic interaction. For example, when the antigen is a recombinant protein which comprises a poly-histidine (poly-HIS) amino acid sequence, the poly-HIS region can interact with the chelated metal ion. When the antigen is a protein, the poly-HIS amino acid sequence may be located at the carboxyl or amino terminus, or an internal region of the protein which does not significantly alter the naturally occurring tertiary or quartenary structure of the protein.

Also provided is a method for producing an adjuvant comprising the steps of preparing a chitosan solution, chelating a metal ion to the chitosan to produce a metal/chitosan complex, and isolating the metal/chitosan complex. Comprehended are methods which include a metal ion which may be, but is not limited to, iron or a transition metal such as copper, zinc, or nickel.

The invention also provides a method for producing an immunogen comprising the steps of preparing a chitosan solution, chelating a metal ion to the chitosan to produce a metal/chitosan complex, and combining an antigen with the metal/chitosan complex. The metal ion in the immunogen can include, but is not limited to, iron or a transition metal such as copper, nickel, or zinc. The antigen may be, but is not limited to a protein, carbohydrate, lipid, glycoprotein or combination thereof. The protein antigen may be naturally occurring or recombinant. The antigen may be combined to the adjuvant by covalent bonding. Preferred covalent attachment is effected by crosslinking. The preferred agent for crosslinking is glutaraldehyde. The resulting crosslinked immunogen may be particulate or gelatinous, depending on the degree of crosslinking. Alternatively, the antigen may be combined with the adjuvant via ionic interaction. Preferred ionic interaction is effected via a recombinant protein antigen comprising a poly-HIS amino acid sequence which interacts with the chelated metal ion. The poly-sequence on the protein antigen may be located at either the carboxyl or amino terminus of the protein. Alternatively, the poly-HIS region may be located at an internal region of the protein which does not significantly alter the tertiary or quartenary structure of the naturally occurring protein. The resulting immunogen may be administered Also provided by the invention is a method for producing an immunogen comprising the steps of preparing a chitosan solution, combining an antigen with the chitosan to form an antigen/chitosan complex, and chelating a metal ion to the antigen/chitosan complex. The metal in the immunogen may be, but is not limited to, iron or a transition metal, such as copper, nickel, or zinc. In the preferred method, the antigen is covalently attached to the chitosan via crosslinking. The preferred agent to effect the crosslinking is glutaraldehyde. The antigen may be, but is not limited to, a protein, carbohydrate, lipid, glycoprotein or combination thereof. If the antigen is a protein, it may be either naturally occurring or recombinant.

As another aspect, the invention provides a method for potentiating an immune response comprising the steps of mixing an antigen with a chitosan immunopotentiating agent and administering the suspension to an animal. The immune response is characterized by a rapid class switch from IgM to IgG production. The ratio of antigen to chitosan may range from 1:100 to 100:1, but is preferable in the range of 10:1 to 1:10. The chitosan adjuvant may be soluble or insoluble; the insoluble adjuvant being particulate or gelatinous in form. The antigen/chitosan suspension may be administered to the animal orally, intra-nasally, intra-vaginally, intra-rectally, or via intraperitoneal, intravenous, or subcutaneous injection; administration may comprise a single route or a multiplicity of routes. The antigen/chitosan mixture may be administered alone, or in combination with other adjuvants. Immunization may comprise a single administration or multiple administrations.

As another aspect, the invention provides a method for potentiating an immune response comprising the steps of forming an adjuvant comprising chitosan and a chelated metal ion to form a metal/chitosan complex, combining an antigen with the metal/chitosan complex to form an immunogen, and administering the immunogen to an animal. The metal ion component of the immunogen may be, but is not limited to, iron or a transitional metal such as copper, nickel, or zinc. The antigen component of the immunogen may be, but is not limited to a protein, carbohydrate, lipid, or combination thereof. The weight:weight ratio of antigen to chitosan may be 100:1 to 1:100. A preferred ratio is 10:1, as determined by weight of antigen to wet weight of metal/chitosan complex. The antigen may be covalently bonded to the metal/chitosan complex; the preferred method for covalent attachment is via crosslinking. A preferred crosslinking agent is glutaraldehyde and the resulting crosslinked immunogen may be particulate or gelatinous depending on the degree of crosslinking. Alternatively, the antigen my be attached to the adjuvant via ionic interaction. A preferred method for attachment with ionic interaction is through use of a recombinant protein antigen comprising a poly-HIS amino acid sequence, the poly-HIS sequence be capable of interacting with the chelated metal ion. The poly-HIS region of the protein may be carboxyl or amino terminal to the protein, or may be internal to the protein in such a manner as to not significantly alter the naturally occurring tertiary or quaternary structure of the protein. The immunogen may be administered to the animal orally, intra-nasally, intra-vaginally, intra-rectally, or via intraperitoneal, intravenous, or subcutaneous injection; administration may comprise a single route or a multiplicity of routes. The immunogen suspension may be administered alone, or in combination with other adjuvants. Immunization may comprise a single administration or multiple administrations.

In another aspect of the invention, a composition is provided which, when administered to an animal, will potentiate an immune response, the composition comprising a conjugate between a protein and chitosan. The chitosan component may be soluble or insoluble; the insoluble adjuvant being gelatinous or particulate in form, depending on the method by which the antigen is combined with the adjuvant. Conjugation may be effected through chemical crosslinking, ionic interaction, physical intercalation, or covalent attachment. The ratio of protein to chitosan may range from 1:100 to 100:1, but is preferable in the range of 1:4 to 1:10. The resulting composition is suitable for administration orally, intra-nasally, intra-vaginally, intra-rectally, or via intraperitoneal, intravenous, or subcutaneous injection.

In another aspect of the invention, a composition is provided which, when administered to an animal, will potentiate an immune response, the composition comprising a suspension of a protein and chitosan. The ratio of protein to chitosan may range from 1:100 to 100:1, but is preferable in the range of 1:4 to 1:10. The resulting composition is suitable for administration orally, intranasally, intravaginally, intrarectally, or via intraperitoneal, intravenous, or subcutaneous injection.

In another aspect of the invention, a method is provided for preparing a compound which potentiates an immune response, wherein an antigen is conjugated to a chitosan adjuvant, the resulting conjugate thereafter being suitable for administration to an animal. Conjugation may be effected through chemical crosslinking, ionic interaction, physical intercalation, hydrophobic interactions, hydrophilic interactions, or covalent attachment. The ratio of protein to chitosan may range from 1:100 to 100:1, but is preferable in the range of 1:4 to 1:10.

In another aspect of the invention, a method is provided for preparing a compound which potentiates an immune response, wherein an antigen is mixed with a chitosan adjuvant to form a suspension which can subsequently be administered to an animal. The ratio of protein to chitosan may range from 1:100 to 100:1, but is preferable in the range of 1:4 to 1:10.

DETAILED DESCRIPTION OF THE INVENTION

The present invention is illustrated by the following examples relating to a method of immunopotentiation which utilizes a protein/chitosan conjugate or a protein/chitosan suspension, as well as methods to prepare the conjugate and/or suspension. In particular, Example 1 relates to the preparation of chitosan particles with an intercalated antigen. Example 2 addresses conjugation of an antigen to chitosan particles. Example 3 describes a general immunization protocol. Example 4 relates an enzyme linked immunosorbent assay (ELISA) utilized in all measurements to determine serum antibody titer. Example 5 describes a comparative analysis of the ability of chitosan to stimulate an immune response to that of other frequently employed adjuvants. Example 6 demonstrates the ability of chitosan to stimulate macrophages in vitro. Example 7 relates to chitosan immunopotentiation as a function of route of administration. Example 8 provides a comparison of the ability of chitosan to stimulate an immune response to that of commercially available adjuvants. Example 9 describes chitosan immunopotentiation as a function of form of the antigen/chitosan association. Example 10 relates preparation of a metal/chitosan complex adjuvant. Example 11 addresses immunopotentiation with a porcine zona pellucida protein combined with various metal/chitosan adjuvants. Example 12 demonstrates use of a zinc/chitosan adjuvant with another porcine zona pellucida protein. Example 13 describes preparation of an iron/chitosan adjuvant. Example 14 addresses palmitylation of a metal/chitosan complex. Example 15 describes the immune response with and without palmitylation of the metal/chitosan adjuvant.

EXAMPLE 1

Preparation of Chitosan Associated Antigen

While the following procedure is exemplified in terms of formulating a chicken albumin/chitosan immunogen, those of ordinary skill in the art will readily appreciate that any of a number of other antigens can be employed.

A 2% solution of practical grade chitosan (Sigma, St. Louis, Mo.), derived from crab shells, was prepared in 0.5 N sodium acetate at pH 5.0. Approximately 10–14 mg albumin was dissolved in 4–5 ml 0.5 M sodium acetate buffer, pH 5.0, and 2 ml of the 2% chitosan solution. This antigen/chitosan mixture was added drop by drop to a beaker containing 25 ml 2-butanol, saturated with sodium acetate, with simultaneous stirring and sonication. After mixing, 2 ml 1 N NaOH was added one drop at a time to the mixture and sonication continued for 1–3 minutes. The resulting emulsion was transferred to a 50 ml beaker and cooled on ice for 5 minutes with occasional shaking. The emulsion was separated by centrifugation with a IEC centrifuge at setting #6 (International Equipment Company, Needham Heights, Me.) for 3–5 minutes, the top butanol layer was discarded, and 25 ml sterile phosphate buffered saline (PBS) was added to the aqueous layer which included the interface precipitate. The resulting emulsion was thoroughly mixed and the chitosan-antigen particles pelleted by centrifugation for 3–5 minutes. The supernatant was decanted and the pellet washed two times, each with 25 ml PBS. The wash solution was decanted, 25 ml PBS was added and the resulting suspension was mixed thoroughly. The suspension was continually sonicated as 20 $\mu$l 25% glutaraldehyde (Sigma, St. Louis, Mo.) was added. After 2 minutes sonication, 15 ml cold, sterile PBS was added and the suspension was cooled on ice for 5–10 minutes. The chitosan associated antigen particles were pelleted by centrifugation for 5 minutes, the supernatant decanted, and the resulting pellet washed three times with 25 ml sterile PBS. The supernatant from the final wash was decanted and the pellet resuspended in 2–3 ml sterile PBS, and thoroughly mixed. This suspension of chitosan associated antigen was either used for immunization or subjected to further modification as described in Example 2.

Antigen/chitosan particles prepared by this method comprise antigen intercalated and crosslinked generally within the porous structure of the chitosan particles.

EXAMPLE 2

Conjugation of Peptide Antigen to Chitosan Particles

While the following procedure is exemplified in terms of formulating an chicken ovalbumin/chitosan immunogen, those of ordinary skill in the art will readily appreciate that any of a number of other antigens can be employed.

In order to covalently attached antigen to the surface of chitosan particles, the chitosan particle/antigen suspension obtained from Example 1 was subjected to the following modification. A 1.667 $\mu$l aliquot of 5 mg/ml N-succinimidyl-3-(2-pyrydyldithio) propionate (SPDP) Pierce Chemical Company, Rockford, Ill.) in dimethylsulfoxide (DMSO) (Sigma) was added to 1 ml of the suspension and allowed to react with the chitosan particles for at least 30 minutes, and usually up to one hour, with occasional mixing. The suspension was centrifuged and the supernatant decanted. The pellet was washed three times with 1 ml PBS and after the last wash, the suspension was centrifuged and the PBS discarded. An albumin solution (1 ml at a approximately 1–2 mg peptide/ml) was added to the pellet, the suspension sonicated, and the mixture allowed to react overnight with gentle mixing at room temperature. Following overnight incubation, the suspension was centrifuged for 5 minutes and the supernatant decanted. The pellet was washed three times with 1 ml PBS per wash. Following the last wash, the suspension was centrifuged and the supernatant discarded. PBS (approximately 1 ml) was added and the suspension sonicated. The final suspension was stored at 4° C. until use.

EXAMPLE 3

Immunization Protocol

Unless otherwise stated in the examples, the following immunization protocol was employed throughout.

Mice were immunized generally with variable amounts of antigen in a 100 µl volume either via intraperitoneal, subcutaneous or intramuscular injection with desired recombinant protein complexed with metal chitosan. Prior to the initial immunization, animals were bled to obtain control serum. After the initial immunization, animals were bled at weekly intervals and antigen titer determined by ELISA as described in Example 4. All animals were boosted with an injection identical to the initial immunogen three to four weeks after the initial immunization.

EXAMPLE 4

Enzyme Linked Immunosorbent Assay (ELISA)

Assessment of the degree to which chitosan, in combination with an antigen, is able to enhance an immune response was made utilizing an enzyme linked immunosorbent assay (ELISA) well known in the art. The protocol employed was as follows.

Flat bottom polyvinyl chloride 96 well assay plates (Falcon #3912) were coated overnight at 4° C. with antigen (50 µl/well at 5–10 µg/ml) in carbonate-bicarbonate buffer, pH 9.6. The plates were washed with PBS containing 0.5% polyoxyethylene (20) sorbitan monolaurate (Tween 80) (Mallinckrodt Specialty Chemical Company, Paris KY) (PBS-T) and post-coated with PBS-T containing 2% non-fat dry milk (PBS-NFDM) for two hours at room temperature to inhibit nonspecific binding. Following three washes with PBS-T, 50 µl of sample or control serum diluted in PBS-T was added to each well, the plates were covered and incubated for 1 hr at room temperature. The plates were emptied, washed three times with PBS-T and 50 µl of a 1:1000 dilution of biotin labelled goat anti-mouse IgG (including both heavy and light polypeptide chains) (Zymed Laboratories, South San Francisco, Calif.) or biotin labelled goat anti-mouse IgM (Southern Biotechnology Associates, Birmingham, Ala.) in PBS-T was added to each well. After 1 hr at room temperature the plates were washed with PBS-T and 50 µl of PBS-T containing horseradish peroxidase conjugated avidin biotin complex from a Vectastain ABC kit (Vector Laboratories, Inc., Burlingame, Calif.). The enzyme substrate was 50 µl of 400 µg/ml o-phenylenediamine (Sigma). Plates were allowed to develop in the dark at room temperature for 20 min. The optical density (OD) at 450 nm was read on a Dynatec Laboratories MR 700 (Chantilly, Va.), using water as a blank.

EXAMPLE 5

Comparative immunopotentiation with Chitosan Associated Antigen

In order to determine the relative degree to which chitosan is able to effect immunopotentiation, a comparative study was undertaken wherein groups of mice were individually immunized with chicken ovalbumin in combination with either chitosan (prepared as described in Example 1), phosphate buffered saline (PBS), Freund's Complete and Incomplete Adjuvant (CFA and IFA, respectively) (Sigma, St. Louis, Mo.), phospholipid complex (PLC) (Emulsigen; MVP Laboratories, Ralston Neb.), glucosaminylmuramyl dipeptide (GMPD) (C. C. Biotech Corp., Poway, Calif.), aluminum hydroxide gel adjuvant (alum) Seargent Pulp and Chemical Co., Clifton, N.J.) or gelatin (Knox Gelatine, Englewood Cliffs, N.J.). Serum titers were determined by ELISA from blood collections as described in Example 3.

Mice were immunized by intraperitoneal injection on Day 1 with the compositions set out in Table 1. Each group contained 3 mice except Group 7 which contained only one. In addition, 2 mice from Group 5 died after the first injection. In each group, a secondary injection, identical to the primary injection unless otherwise noted, was administered on the 21st day after the primary injection. Blood was collected from the mice on three occasions: i) 21 days after the first injection; ii) 31 days after the first injection; and iii) 43 days after the first injection.

TABLE 1

Immunization Protocol

| Group | Immunization Composition | Dosage/mouse |
|---|---|---|
| 1 | Chitosan particles with chicken ovalbumin* | 40–60 µl |
| 2 | Chicken ovalbumin** in PBS | 80–100 µl |
| 3 | Primary Injection: | 80–100 µl |
|   | 50% CFA with chicken ovalbumin** in PBS |   |
|   | Secondary Injection: |   |
|   | 50% IFA with chicken ovalbumin** in PBS |   |
| 4 | 5% PLC with chicken ovalbumin** | 80–100 µl |
| 5 | GMDP with chicken ovalbumin** | 50–80 µl |
|   | Composition: |   |
|   | 20 µl 5 mg/ml chicken ovalbumin in PBS |   |
|   | 1 µl 10 mg/ml GMDP |   |
|   | 21 µl mineral oil |   |
|   | 8 µl Pluronic L-121# |   |
|   | 1 µl Tween 80 |   |
| 6 | 20% Alum with chicken ovalbumin** | 80–100 µl |
| 7 | Chicken ovalbumin** in 3% gelatin | 80–100 µl |

\* Final ovalbumin concentration 2 mg/ml
\*\* Final ovalbumin concentration 1 mg/ml
\# Obtained from BASF, Wyanodette Corp, Parsipany, NJ (Described in U.S. Pat. 4,772,466)

Antibody production in response to the immunizations described were measured by ELISA and the results from the first two bleeds are shown in Table 2.

TABLE 2

Serum Antibody Levels ($OD_{490}$)

| GROUP | BLEED | FOLD SERUM DILUTION | | |
|---|---|---|---|---|
|   |   | 250 | 1250 | 6250 |
| 1 | Primary | 0.20 | 0.13 | 0.05 |
|   | Secondary | 0.25 | 0.19 | 0.12 |
| 2 | Primary | 0.00 | 0.03 | 0.00 |
|   | Secondary | 0.00 | 0.00 | 0.00 |
| 3 | Primary | 0.10 | 0.07 | 0.09 |
|   | Secondary | 0.17 | 0.15 | 0.12 |
| 4 | Primary | 0.00 | 0.00 | 0.00 |
|   | Secondary | 0.06 | 0.03 | 0.00 |
| 5 | Primary | 0.02 | 0.00 | 0.00 |
|   | Secondary | 0.14 | 0.08 | 0.02 |
| 6 | Primary | 0.00 | 0.00 | 0.00 |
|   | Secondary | 0.06 | 0.02 | 0.01 |
| 7 | Primary | 0.00 | 0.00 | 0.00 |
|   | Secondary | 0.07 | 0.02 | 0.01 |

These results indicated that chitosan prepared as described in Example 1 enhances the immune response greater than the other more commonly employed adjuvants when administered via intraperitoneal injection. Endpoint titration by ELISA (Table 3), utilizing a different spectrophotometer, gave results consistent with the results shown in Table 2. Endpoint measurements in Table 3 can generally be considered to be values below 0.20.

TABLE 3

End Point Titration of Serum Antibody Levels

| GROUP | BLEED (days post injection) | FOLD SERUM DILUTION | | | | | | | | |
|---|---|---|---|---|---|---|---|---|---|---|
| | | 500 | 1k | 2k | 4k | 8k | 16k | 32k | 64k | 128k |
| 1 | 21 | 0.74 | 0.53 | 0.38 | 0.26 | 0.21 | 0.16 | 0.13 | 0.13 | 0.12 |
| | 31 | 1.24 | 0.98 | 0.75 | 0.53 | 0.42 | 0.27 | 0.23 | 0.18 | 0.15 |
| | 43 | 1.44 | 1.21 | 1.01 | 0.78 | 0.51 | 0.36 | 0.26 | 0.20 | 0.15 |
| 2 | 21 | nd | nd | nd | nd | nd | nd | nd | nd | nd |
| | 31 | 0.13 | 0.12 | 0.12 | 0.12 | 0.11 | 0.12 | 0.12 | 0.13 | 0.12 |
| | 43 | 0.14 | 0.13 | 0.13 | 0.12 | 0.12 | 0.13 | 0.12 | 0.12 | 0.12 |
| 3 | 21 | 0.33 | 0.30 | 0.25 | 0.22 | 0.19 | 0.16 | 0.14 | 0.13 | 0.13 |
| | 31 | 0.66 | 0.59 | 0.52 | 0.48 | 0.37 | 0.30 | 0.24 | 0.20 | 0.16 |
| | 43 | 0.79 | 0.65 | 0.53 | 0.50 | 0.41 | 0.32 | 0.26 | 0.21 | 0.17 |
| 4 | 21 | nd | nd | nd | nd | nd | nd | nd | nd | nd |
| | 31 | nd | nd | nd | nd | nd | nd | nd | nd | nd |
| | 43 | 0.19 | 0.20 | 0.18 | 0.18 | 0.19 | 0.18 | 0.18 | 0.17 | 0.16 |
| 5 | 21 | 0.15 | 0.14 | 0.14 | 0.14 | 0.14 | 0.13 | 0.12 | 0.12 | 0.13 |
| | 31 | 0.40 | 0.36 | 0.28 | 0.22 | 0.19 | 0.18 | 0.15 | 0.13 | 0.13 |
| | 43 | 0.34 | 0.29 | 0.20 | 0.19 | 0.18 | 0.16 | 0.18 | 0.13 | 0.12 |

EXAMPLE 6

Chitosan Stimulation of Macrophages In Vitro

In view of the observation that various soluble and insoluble derivatives of chitin activate peritoneal macrophages in vivo, [Nishimura, et al. supra], assays were conducted to determine if particulate chitosan possesses the same biological property.

Peritoneal macrophages were isolated from both untreated BALB/c mice and mice treated with known macrophage activators. The macrophage activators used were mineral oil, starch, and polycarbophil (B.F. Goodrich Company, Breaksville, Ohio). Macrophages were removed from the mouse peritoneal cavities by washing with RPMI, collected in siliconized tubes and washed three time with Hank's Buffered Saline Solution (HBSS). Washed cells were than allocated into tubes with either chitosan beads containing ovalbumin, carboxy fluorescene, or fluoroisothiocyanate (FITC) labeled *Staphylococcus aureus* prepared as described in Example 1. Carboxy fluorescene and FITC wells did not contain ovalbumin antigen. Macrophage and antigen were allocated into a 96 well plate following a one hour incubation in a small siliconized tube. Observations were done at different time points using a fluorescent microscope under both visible and ultraviolet light.

Ovalbumin/chitosan particles did not fluoresce, indicating that chitosan alone does not fluoresce. Within five hours, fluorescent chitosan particles could be seen in all macrophage cultures containing carboxy fluorescene or FITC-labeled *S. aureus,* including those that had not been pre-activated. At thirty hours, diffuse fluorescent staining of macrophage in culture could be seen. This observation suggests that the protein/chitosan particles were being phagocytized and digested in vitro by peritoneal macrophages regardless of whether they were pre-activated. Preliminary data also suggested that the phagocytized antigen is then processed.

EXAMPLE 7

Immunopotentiation as a Function of Route of Administration

In order to assess the influence of route of administration of antigen/chitosan on stimulated antibody production, immunogens were administered to mice via either intraperitoneal injection, oral ingestion or rectal deposition.

For all routes of administration, ovalbumin/chitosan particles were prepared as described in Example 1. For intraperitoneal injection, mice were immunized one time with 100 µg ovalbumin. For oral and rectal administration, mice were immunized with 100 µg ovalbumin on the same day as the mice that received intraperitoneal immunizations, in addition to a second immunization two days later with the same ovalbumin dosage.

The level of stimulated antibody production as a function of these various routes of administration, as determined by ELISA described in Example 3, are set forth in Table 4.

TABLE 4

Induction of Immune Response by Different Routes of Administration ($O.D._{490}$)

| | Intraperitoneal | | | Oral | Rectal |
| | | | | | |
| Serum Dilution | Adjuvant Only | Adjuvant and Antigen Mixed | Antigen in Chitosan beads | Antigen Only | Antigen in Chitosan beads | Antigen in Chitosan beads |
|---|---|---|---|---|---|---|
| 1:10 | .035 | .102 | .586 | .053 | .553 | .190 |
| 1:50 | .027 | .032 | .296 | .054 | .112 | .026 |
| 1:250 | .022 | .023 | .137 | .026 | .080 | .036 |

Background titer determined for antigen alone following intraperitoneal injection was consistent between experiments and did not vary significantly as a function of route of administration.

These results indicated that administration of ovalbumin in chitosan beads by either intraperitoneal, oral, or rectal routes of administration effects comparable levels of serum antibodies in mice. In addition, simple mixing of antigen and chitosan beads, or chitosan beads and antigen administered in the separate site (data not shown) did not induce a comparable level of antibody production to that induced by antigen encapsulated, or intercalated, in chitosan particles. These results were particularly surprising in view of previous reports that oral administration of insoluble chitosan is ineffective in potentiating the immune response (Marcinkiewicz, et al., supra).

EXAMPLE 8

Comparison of Chitosan Immunopotentiation Against Commercially Available Adjuvants The ability of chicken ovalbumin (OVA) to elicit an immune response in mice was determined after immunization with antigen/chitosan particles prepared as described in Example 1, or ovalbumin administered together with other commercially available adjuvants. Administration was effected via both intraperitoneal and subcutaneous injection. Antibody titers, including both IgG and IgM, were measured at the number of days following a single immunization as indicated in Table 5. The protocol for this study is as follows.

Six week old BALB/c mice (3 per group) were immunized by the intraperitoneal or subcutaneous route with 200 µg of chicken egg albumin (Sigma, St. Louis, Mo.) in each adjuvant tested. Ovalbumin/adjuvant formulations were prepared according to manufacturers' suggested protocols.

Specifically, for each injection 100 µl of Complete Freund's Adjuvant (CFA; Sigma) was mixed with 100 Al of sterile phosphate buffered saline (PBS) containing 200 µg of OVA and sonicated until a stable emulsion was formed. Each mouse received 200 µl of this CFA formulation.

Ribi Immunochem Research, Inc.'s MPL+TDM+CWS—Ribi Adjuvant System (RAS) (Sigma Immunochemicals) was prepared by mixing 100 µl of warmed reconstituted adjuvant with 100 Al of sterile PBS containing 200 µg of ovalbumin. Each mouse received 200 µl of this formulation.

Hunter's TiterMax Adjuvant was also obtained through Sigma Immunochemicals. Each dose was prepared by mixing 25 µl of adjuvant with 25 µl of sterile PBS containing 200 µg of ovalbumin and sonicating until a stable emulsion was formed. Each mouse received 50 µl of this formulation.

AdjuPrime Immune Modulator was obtained from Pierce (Rockford, Ill.) and prepared using the manufacturer's suggested dry antigen protocol. AdjuPrime powder was mixed with ovalbumin powder at a 1:15 (w/w) antigen:AdjuPrime ratio and finely ground between sheets of weighing paper with the bottom of a flask until homogeneous. This mixture was then reconstituted with sterile PBS to a final ovalbumin concentration of 1 µg/µl. The final immunizing dose was therefore 200 µl containing 200 µg of ovalbumin. Identical booster immunization preparations were stored frozen at −20° C. until required.

Ovalbumin/chitosan immunogen was prepared as described in Example 1. Antibody titer was determined by ELISA as described in Example 3.

Experimental groups were immunized with ovalbumin and the adjuvant as follows: Group 1, intraperitoneal injection with AdjuPrime Immune Modulator; Group 2, intraperitoneal injection with PBS; Group 3, intraperitoneal injection with chitosan; Group 4, intraperitoneal injection with Ribi Adjuvant System; Group 5, intraperitoneal injection with TiterMax; Group 6, intraperitoneal injection with Complete Freund's Adjuvant; Group 7 subcutaneous injection with Complete Freund's Adjuvant; Group 8, subcutaneous injection with PBS; Group 9, subcutaneous injection with chitosan; Group 10, subcutaneous injection with Ribi Adjuvant System; Group 11, subcutaneous injection with TiterMax. Data obtained (determined as the geometric mean titer of IgM anti-ovalbumin antibody production by each group of mice at 7 days post immunization) indicate that chitosan associated antigen poorly stimulates early (day 7) IgM antibody production. It should be noted that many of the other adjuvant preparations resulted in higher levels of IgM antibody production. In contrast, as evidenced by the geometric mean titer of IgG anti-ovalbumin antibody data (data was obtained from immunized as described above with respect to IgM), chitosan associated antigen stimulates more rapid and higher levels of IgG antibody production by mice. This result indicates that antigen associated with chitosan more quickly stimulates immunoglobulin class switching to B cells which do not produce IgM. Because memory B cells produce IgG, rapid and elevated levels of IgG production suggests that chitosan association may result in enhanced immunologic memory.

The total antibody titers on days 21, 28, and 35 following a single intraperitoneal injection of 200 µg ovalbumin in each adjuvant are presented in Table 5. Values represent geometric mean titer from treatment groups containing three mice. Note that many immunization protocols call for booster immunization at 21 days post immunization (dpi) and that the antibody response induced by chitosan associated ovalbumin at 21 dpi was superior to all other adjuvant formulations regardless of the route of administration. Similar results were obtained following a single subcutaneous injection. The results are set out in Table 6, wherein values are geometric means titers from groups of three individual mice.

TABLE 5

Comparative Immunopotentiation - Intraperitoneal Injection

| ADJUVANT | 21 dpi | 28 dpi | 35 dpi |
| --- | --- | --- | --- |
| PBS | 27 | 320 | 100 |
| Chitosan | 2240 | 10240 | 20480 |
| Ribi | 747 | 933 | 173 |
| Titer Max | 853 | 9387 | 14520 |
| AdjuPrime | 853 | 1920 | 4270 |
| CFA | 747 | 14507 | 20480+ |

TABLE 6

Comparative Immunopotentiation - Subcutaneous Injection

| ADJUVANT | 21 dpi | 28 dpi | 35 dpi |
| --- | --- | --- | --- |
| PBS | 640 | 27 | 97 |
| Chitosan | 9387 | 5973 | 12800 |
| Ribi | 533 | 80 | 187 |
| Titer Max | 80 | 6987 | 7254 |
| CFA | 640 | 20480 | 20480+ |

EXAMPLE 9

Immunopotentiation as a Function of the Nature of Chitosan/Antigen Association In order to determine the effect of the form of the protein/chitosan association has on immunopotentiation, a study was performed wherein protein/chitosan adjuvant prepared by various methods was administered to mice. In one case, the immunogen was prepared as described in Example 1 (Group 1). In another case, chitosan particles were prepared as described in Example 1, except that no antigen was utilized in the preparation (Group 2). In still another case, antigen was prepared as described in Example 1, except that no chitosan was utilized in the preparation. In this last case, chitosan particles were added to albumin antigen prepared as described in Example 1 (Group 3). The immunization protocol was as follows.

Nine BALB/c mice were divided into three groups of three mice (n=3). Each group received intraperitoneal injections of 100 μg of antigen. The first group received antigen comprising 100 μg ovalbumin together with 200 μg chitosan particles prepared as described in Example 1. The second group received only 100 μg ovalbumin particles prepared using the same method. The third group received a simple mixture of 100 μg ovalbumin particles and 200 μg chitosan particles. The geometric mean anti-ovalbumin antibody titers of these groups of mice at 21 dpi as determined by ELISA are presented in Table 7.

TABLE 7

Immunopotentiation as a Function of Antigen/Chitosan Association

| GROUP | TREATMENT | 21 dpi |
|---|---|---|
| 1 | Ovalbumin coupled to chitosan | 747 |
| 2 | Ovalbumin particles alone | 40 |
| 3 | Ovalbumin and chitosan mixed | 33 |

The results of this experiment are informative because they establish that the observed adjuvant activity is not due simply to physio-chemical alterations in the ovalbumin resulting from its particulation during the chitosan coupling procedure. These findings also indicate that the adjuvant activity of ovalbumin/chitosan preparations results from their conjugation and that coupling is required for maximal activity.

These results, therefore, are distinct from those described by Marcinkiewicz, et al., [supra] and Suzuki et al. [supra] as neither of these groups reported a need or advantage to conjugation of the antigen to chitosan. These groups applied chitosan as a nonspecific immunostimulator of macrophages, by either pretreating with a series of chitosan injections or administering it at the same time as antigen. Results set out in Example 5 are consistent with these previously reported observations, indicating activation of peritoneal macrophages and the phagocytosis of chitosan associated fluorescent antigen (data not shown). More importantly, however, the results in Table 7 show that covalent association of particulate or gelatinous chitosan and antigen are required for the maximal induction of antibody production by our mice.

Additional distinctions exist between these results and the work of Marcinkiewicz, et al. [supra] and Suzuki et al., [supra]. Both groups used Jerne hemolytic plaque assays to quantitate the IgM antibody producing plaque forming cells (PFC) in the spleen. Herein, however, total antibody levels in the serum were measured, in addition to concentration of both IgG and IgM isotype antibodies. Marcinkiewicz, et al., and Suzuki, et al., also describe the PFC response to Sheep Red Blood Cells (SRBC), a particulate antigen, whereas the present invention has been exemplified utilizing chicken ovalbumin, a soluble antigen, in association with insoluble chitosan particles. Marcinkiewicz, et al. and Suzuki, et a., reported the efficacy of only intraperitoneal route of injection; herein successful immunopotentiation was obtained using both intraperitoneal and subcutaneous routes of injection.

As previously stated, the results shown above in Table 7 are serum titers determined for an antigen covalently associated with a particulate or gelatinous form of chitosan. In another experiment using soluble chitosan, opposite results were obtained. Briefly, a 1 % chitosan solution in acetic acid was prepared as described and mixed with heat denatured total porcine zona pellucida protein. The pH of the mixture was raised to 6.8 using NaOH and approximately 200 μg antigen was injected subcutaneously into mice. Results indicated that serum titer for zona proteins was higher when the antigen was not crosslinked to the soluble chitosan than when the antigen/chitosan was crosslinked using glutaraldehyde. In addition, the immune response was much more rapid in the absence of crosslinking.

EXAMPLE 10

Preparation of Metal/Chitosan Complexes Containing Either Zinc, Copper, or Nickel Previous observations during the purification of poly-HIS-tagged zona pellucida (ZP) proteins using nickel (Ni)-Sepharose chromatography suggested that sperm readily bound to the Ni-immobilized ZP proteins as compared to the binding detected with ZP proteins immobilized on other affinity columns. This observation is of particular interest because ZP proteins play a role in sperm binding to oocytes. This observation suggested that the poly-HIS-tagged ZP proteins may be capable of maintaining a more natural conformation when immobilized by this method. This observation, when combined with a previous observation that chitin possesses the ability to chelate transition metal ions, led to an investigation of the possible use of a metal/chitosan chelate for binding a poly-HIS-tagged antigen and its use as an immunopotentiator. Given that transition metal ions are toxic in general, several different ions were initially tested to produce the metal/chitosan complexes.

To prepare chitosan/metal complex adjuvants containing either zinc, copper or nickel, a 2% chitosan solution was initially prepared by dissolving 2 g chitosan (CTC Organics, Atlanta, Ga.) in 100 ml 2% acetic acid, the resulting solution sterilized by autoclaving. As an alternative, the chitosan solution can also be prepared by dissolving 2 g in 100 ml 0.5 M sodium acetate pH 4.5. A zinc acetate, nickel sulfate or copper sulfate solution was prepared in deionized water at a molarity between 0.001 to 0.2 M and filter sterilized. The 2% chitosan solution was diluted 1:1 using deionized water and 4 ml of the resulting 1 % chitosan solution was added to 10 ml of the desired metal salt solution. The resulting suspension was mixed on an end to end shaker for 2 to 4 hours at room temperature. The mixture was sonicated using a Branson Sonifier 250 for 3 to 5 minutes and the pH of the mixture adjusted to 12.0–12.5 with 10 N NaOH during sonication. When the zinc salt was employed, a white complex precipitate was formed, when the nickel salt was used, the complex was light green and when the copper salt was used, the complex was blue. After sonication, the mixture was centrifuged at 2000 rpm (1000×g) for 10 minutes and supernatant discarded. The pellet was washed twice with PBS, pH 7.2, centrifuged after each wash, the wet weight of the pellet determined, and the metal/chitosan complex pellet resuspended in 8 M urea, pH 7.8 to 8.0. The metal/chitosan complexes were either immediately coupled to an antigen, or stored in either 8 M urea or PBS at room temperature. The stored metal/chitosan complexes have shown to be stable for up to six months when stored by this method.

Antigens were associated with the metal/chitosan complex by one of two alternative methods. In the first method, proteins were crosslinked to the metal/chitosan complex using glutaraldehyde as previously described in Example 13 and the following example. In another method, (described in this example), recombinant proteins contained a C-terminal poly-histidine region to facilitate purification and to permit association of the protein with the metal component of the metal/chitosan complex. This procedure is described as follows.

Recombinant proteins modified to include six histidines (poly-HIS) were expressed in either bacteria, yeast, insect, or CHO cells and purified using Ni-Sepharose or cobalt (Co)-Sepharose chromatography both of which are well known in the art. Recombinant protein was equilibrated in 8 M urea and incubated with the chitosan metal complex in a plastic tube for 1 to 3 hours at room temperature. Following incubation, protein/metal/chitosan complex was pelleted by centrifugation for 10 minutes at 1000×g and the amount of complex bound protein estimated by determining protein concentration in the supernatant following centrifugation and subtracting the amount initially added to the binding reaction. In general, the resulting ratio of mg antigen:mg wet weight metal/chitosan averaged 10:1. The pellet was washed two times with PBS, resuspended in PBS and the concentration adjusted to 1 mg antigen/ml buffer.

Specific use and results from the use of an antigen/zinc/chitosan as an immunogen are described below in Examples 11 and 12.

EXAMPLE 11

Immune response To Recombinant Pig Zona Pellucida Protein B (Pig-b) Complexed With Chitosan Complexed With Either of Nickel, Copper or Zinc Recombinant porcine zona pellucida protein pig-b, expressed in bacteria, was complexed to either nickel/chitosan, copper/chitosan, or zinc/chitosan as described above in Example 10. Individual groups of mice were immunized intraperitoneally with either 5, 25, 100 or 250 µg protein/mouse in case of nickel/chitosan and zinc/chitosan, or either 5 or 25 µg protein/mouse in case of copper/chitosan. Each group received a booster immunization on day 21 after the initial immunization with the same amount of antigen and metal/chitosan. Mice were bled on day 8, 21, 28 and 49 after the first immunization and serum titer determined by ELISA as described above in Example 4. Serum titers determined against bacterially expressed zona pellucida pig b and heat solubilized total native pig zona are shown in Tables 8 and 9, respectively. These results suggest little difference between the chelate adjuvants in terms of immunopotentiation.

TABLE 8

Serum Titer Determined By ELISA Using Recombinant Pig-C

| Day | Dose/mice (µg)- | | | |
|---|---|---|---|---|
| | 5 | 25 | 100 | 250 |
| Pig-B Nickel-chitosan | | | | |
| 8 | 200 | 100 | 800 | 3.2K |
| 21 | 4k | 16k | 32k | 8k |
| 28 | 32k | 64k | >64k | >64k |
| 49 | 16k | 64k | >64k | >64k |
| Pig-B Zinc-chitosan | | | | |
| 8 | 200 | 100 | 800 | 3.2K |
| 21 | 16k | 32k | 64k | >64k |
| 28 | >64k | >64k | >64k | >64k |
| 49 | 32k | >64k | >64k | >64k |
| Pig-B Copper-chitosan | | | | |
| 8 | 400 | 200 | ND* | ND* |
| 21 | 2k | 2k | ND* | ND* |
| 28 | 32k | 32K | ND* | ND* |

*ND - dose not done

TABLE 9

Serum Titer Determined By ELISA Using Heat-Denatured Total Zona Pellucida Protein

| Day | Dose/mice (µg)- | | | |
|---|---|---|---|---|
| | 5 | 25 | 100 | 250 |
| Pig-B Nickel-chitosan | | | | |
| 8 | 200 | 200 | 800 | 400 |
| 21 | 500 | 1k | 4k | 4k |
| 28 | 4k | 8k | 16k | 16k |
| Pig-B Zinc-chitosan | | | | |
| 8 | 200 | 200 | 200 | 3.2 |
| 21 | 500 | 2k | 32k | 8k |
| 28 | 8k | 16k | >64k | >64k |
| Pig-B Copper-chitosan | | | | |
| 8 | 800 | 1.6k | ND* | ND* |
| 21 | 500 | 1k | ND* | ND* |
| 28 | 1k | 4k | ND* | ND* |

*ND - dose not done

EXAMPLE 12

Immunization With Bacterially Expressed Zona Pellucida Pig-C Protein Complexed with Zinc/Chitosan Balb/c mice were immunized with bacterially expressed recombinant pig zona pellucida C protein (pig-c) and complexed to zinc/chitosan by the following protocol.

The pig-c antigen was initially expressed in and purified from *E. coli* and subsequently complexed with zinc-chitosan prepared as described above in Example 10. Mice were immunized intraperitoneally with 100 µg antigen/mouse (Group I). In one control group (Group II), mice were immunized at 100 µg/mouse with purified protein alone, and in another control group (Group III), mice were immunized with pig-c protein associated with precipitated zinc acetate following the same protocol in Example 10 for making zinc/chitosan except that 1 % chitosan was not added to the solution. The mice were boosted on day 21 with pig-c antigen at 100 µg/mouse complexed with zinc/chitosan by the same preparation used for the initial immunization. Mice were bled on day 21, 28 and 49 by retro-orbital puncture and serum titers were measured by ELISA as described in Example 4. Results are shown in Table 10.

On day 21, serum titer in Group I averaged 64k as compared to titers of less than 250 for Group II and 1k for Group III. After a booster immunization on day 21 following the initial immunization, serum titers determined from bleeds taken on day 28 were found to be more than 64k for Group I, and 4k for both Groups II and III. These data indicate that neither the antigen alone, nor the metal/antigen components of the adjuvant are responsible for the observed immune response, but that the immune response requires the appropriate antigen/metal/chitosan complex for rapid stimulation of an immune response that persists over time.

TABLE 10

Comparison of Immune Response Using Antigen/Metal/Chitosan, Antigen or Antigen/Metal

| | Antigen | | |
|---|---|---|---|
| Days After Immunization | Recombinant Pig-C on Zinc/Chitosan (Group I) | Recombinant Pig-C (Group II) | Recombinant Pig-C Precipitated on Zinc (Group III) |
| 21 | 32k | <250k | 1k |
| 28 | >64k | 8k | 4k |
| 49 | >64k | 4k | 4k |

EXAMPLE 13

Preparation of Chitosan-Metal Complexes Containing Iron

For preparation of an iron/chitosan complex immunogen, 4 g ferric ammonium citrate was dissolved in 10 ml distilled water with 100 µl 11.6 N HCl. Four ml of the 1 % chitosan solution prepared as described above was sonicated and 200 µl of the ferric ammonium citrate solution was added during sonication. The resulting solution was centrifuged and the pellet containing iron/chitosan complex was washed once in deionized water. Recombinant proteins modified to include six histidine residues were coupled the iron/chitosan complex as above except 8 M urea was not added. Alternatively, with proteins such as egg ovalbumin or bacterial/viral proteins which did not include the poly-histidine sequence, the antigen was coupled to the iron/chitosan complex by one of the methods described as follows.

In a first method, iron/chitosan complex was prepared as described above. A protein solution in PBS pH 7.4 was added and the resulting suspension vortexed to obtain a uniform mixture. A 25 % glutaraldehyde solution was diluted 1:4 with PBS and added to the antigen/chitosan mixture at a volume of 20 µl per ml of the antigen/chitosan mixture. The resulting suspension was mixed on an end to end shaker for at least 4 hours. After mixing, 100 µl 1 M glycine in PBS was added to neutralize unreacted glutaraldehyde and incubation continued for 1 hour at room temperature. The mixture was centrifuged for 10 minutes at 1000×g and the resulting pellet washed two times with PBS. After the final wash, the pellet was resuspended at a antigen concentration of 1 mg/ml in PBS and immediately used to immunize animals.

In an alternative to the preceding protocol, 1 % chitosan, prepared as described above and not complexed with iron, was added to a desired protein and the resulting mixture shaken gently to prepare a uniform mixture. As described above, a 25% glutaraldehyde solution was diluted 1:4 with PBS and added to the antigen/chitosan mixture at a volume of 20 µl per ml antigen/chitosan mixture. The resulting solution was incubated at room temperature for approximately 2 to 6 hours to permit limited glutaraldehyde-induced crosslinking, after which time the mixture became a gel. The loosely crosslinked material was generally clear, flowable and did not appear to be particulate when viewed under a microscope. The resulting material was sonicated for 2–3 minutes during which time 400 µl of 4 g/ml ferric ammonium citrate solution was added which induced formation of fine yellowish-brown particles in which the antigen was entrapped. The antigen/iron/chitosan particles were pelleted by centrifugation for 10 minutes at 1000×g and the resulting pellet resuspended at an antigen concentration of about 1 mg/ml. This solution was used to immunize mice by the protocol described in Example 3.

EXAMPLE 14

Preparation of Palmitylated Iron Chitosan

In view of previous reports regarding immune stimulating complex (ISCOM) which have been demonstrated to induce a higher titer when the complex is palmitylated, the following procedure was carried out to modify the antigen/metal/chitosan complex prior to immunization.

Protein antigen was incorporated into iron chitosan particles by any of the method described above and palmitic groups were added by the following procedure. Twenty mg palmitic anhydride was dissolved in 1 ml of triethylamine and the solution added to a protein/metal/chitosan complex solution at a ratio of 10 µl palmitic anhydride for every 1 mg of antigen in the iron/chitosan complex solution. The resulting solution was mixed by gentle tapping and allowed to sit at room temperature for at least two hours before the preparation was diluted and used for immunizations.

EXAMPLE 15

Immunization With Pig-C Incorporated In Iron/chitosan Particles With And Without Palmitylation Purified zona pellucida pig-C protein expressed in *E. coli* was incorporated onto iron/chitosan particles as follows. Ten ml 1 % chitosan solution in 2% acetic acid was sonicated 2–3 minutes with continuous addition of 400 µl 0.4 g/ml ferric ammonium citrate solution during sonication. Resulting iron/chitosan particles were pelleted by centrifugation and the pellet washed two times with deionized water. A solution containing pig-c protein expressed in *E. coli* was adjusted to a pH 7.8 with PBS and incubated with iron/chitosan particles, incubation was allowed to continue overnight with mixing on an end to end shaker. After incubation, the antigen/metal/chitosan particles were pelleted by centrifugation at 1000×g for 10 minutes and protein concentration in supernatant measured by the Bradford method known in the art. The final ration of antigen to metal/chitosan was determined to be 3.7 mg pig-c protein bound per gram wet weight iron-chitosan. Prior to use as immunogen, the pig-c iron was adjusted to a concentration of 1 mg antigen/ml.

In order to produce a palmitylated pig-c/iron/chitosan immunogen, particles produced as described above were initially incubated in 8 M urea. A solution of 20 mg palmitic anhydride was prepared in 1 ml triethylamine, and 10 µl of the solution was added to 1 mg equivalent (protein) pig-c/iron/chitosan. The mixture was shaken gently and allowed to incubate at room temperature for at least 2 hours before use as an immunogen.

Balb/c mice were immunized intraperitoneally with either pig-c incorporated in iron/chitosan particles or palmitylated pig-c/iron/chitosan particles. Individual groups of mice were initially immunized with 100 µg protein and each group was booted on day 22 following the initial immunization with identical dosages and preparations. Mice were bled on day 7, 14, 22, 42, 56 and 63 after the initial immunization and serum antibody titers estimated by ELISA against recombinant pig-c protein. A comparison of the serum titers against pig-c in the both groups are summarized in the Table 3.

Serum titers were comparable in the primary response, but after the booster immunization, serum titer in the group of mice injected with palmitylated antigen was significantly higher (>128k) that determined for the non-palmitylated group (64k).

TABLE 11

Effect of Palmitylation on Metal/Chitosan Immunopotentiation

| Days After Immunization | Preparation | |
|---|---|---|
| | Pig-C/ Iron/Chitosan | Palmitylated Pig-C/ Iron/Chitosan |
| 7 | 400 | 400 |
| 14 | 3.2k | 3.2k |
| 22 | 3.2k | 3.2k |
| 42 | 64k | 128k |
| 56 | 128k | >128k |
| 63 | 64 | >128k |
| 76 | 64k | >128k |

Although the present invention has been described in types of preferred embodiments, it is intended that the present invention encompass all modifications and variations which occur to those skilled in the art upon consideration of the disclosure herein, and in particular those embodiments which are within the broadest proper interpretation of the claims and their requirements.

What is claimed is:

1. An immunogen comprising an antigen in combination with a chitosan/metal ion chelate, wherein the concentration of metal ion ranges from about 0.7 mM to about 143 mM and wherein the metal ion is selected from the group consisting of zinc and transition metals.

2. The immunogen of claim 1, wherein the metal ion is zinc.

3. The immunogen of claim 1, wherein the transition metal is selected from the group consisting of iron, nickel, and copper.

4. The immunogen of claim 1, wherein the antigen comprises a protein.

5. The immunogen of claim 4, wherein the protein comprises a recombinant protein.

6. The immunogen of claim 5, wherein the recombinant protein further comprises a poly-histidine amino acid sequence.

7. The immunogen of claim 6, wherein the poly-histidine amino acid sequence is linked to the carboxyl terminus of the protein.

8. The immunogen of claim 6, wherein the poly-histidine amino acid sequence is linked to the amino acid terminus of the protein.

9. The immunogen of claim 6, wherein the protein is attached to the adjuvant through interaction of the poly-histidine amino acid sequence and the metal ion.

10. A method for stimulating an immune response comprising administering to an animal an immunogen according to any of claims 1–9.

11. A method for producing an immunogen comprising the steps of:
   a) preparing a chitosan solution;
   b) chelating a metal ion to the chitosan to produce a metal/chitosan complex, wherein the concentration of metal ion ranges from about 0.7 mM to about 143 mM and wherein the metal ion is selected from the group consisting of zinc and transition metals; and
   c) combining an antigen with the metal/chitosan complex.

12. The method of claim 11, wherein the metal ion is zinc.

13. The method of claim 11, wherein the transition metal is selected from the group consisting of copper, nickel, and iron.

14. The method of claim 11, wherein the antigen comprises a protein.

15. The method of claim 14, wherein the protein comprises a recombinant protein.

16. The method of claim 15, wherein the recombinant protein further comprises a poly-histidine amino acid sequence.

17. The method of claim 16, wherein the poly-histidine amino acid sequence is linked to the carboxyl terminus of the protein.

18. The method of claim 16, wherein the poly-histidine amino acid sequence is linked to the amino terminus of the protein.

19. The method of claim 16, wherein the protein is attached to the metal/chitosan complex through interaction of the poly-histidine amino acid sequence and the metal ion.

20. The method of claim 11, wherein the chitosan solution is a 1% chitosan solution.

21. The method of claim 20, wherein the 1% chitosan solution is prepared using a solvent selected from the group consisting of acetic acid and sodium acetate.

22. The method of claim 11, wherein step b) further comprises sonication of the metal/chitosan complex.

23. The method of claim 22, wherein step b) further comprises centrifugation of the metal/chitosan complex to form a pellet comprising the metal/chitosan complex.

24. The method of claim 23 further comprising resuspending the resulting pellet.

25. A method for producing an immunogen comprising the steps of:
   a) preparing a chitosan solution;
   b) combining an antigen with the chitosan to form an antigen/chitosan complex; and
   c) chelating a metal ion to the antigen/chitosan complex, wherein the concentration of metal ion ranges from about 0.7 mM to about 143 mM and wherein the metal ion is selected from the group consisting of zinc and transition metals.

26. The method of claim 25, wherein the metal ion is zinc.

27. The method of claim 25, wherein the transition metal is selected from the group consisting of copper, nickel, and iron.

28. The method of claim 25, wherein the antigen comprises a protein.

29. The method of claim 28, wherein the protein comprises a recombinant protein.

30. The method of claim 29, wherein the recombinant protein further comprises a poly-histidine amino acid sequence.

31. The method of claim 30, wherein the poly-histidine amino acid sequence is linked to the carboxyl terminus of the protein.

32. The method of claim 30, wherein the poly-histidine amino acid sequence is linked to the amino terminus of the protein.

33. The method of claim 30, wherein the protein is attached to the metal/chitosan complex through interaction of the poly-histidine amino acid sequence and the metal ion.

34. The method of claim 25, wherein the chitosan solution is a 1% chitosan solution.

35. The method of claim 34, wherein the 1% chitosan solution is prepared using a solvent selected from the group consisting of acetic acid and sodium acetate.

36. The method of claim 25, wherein step b) further comprises sonication of the antigen/chitosan complex.

37. The method of claim 25, wherein step c) further comprises centrifugation of the metal/chitosan/antigen complex to form a pellet comprising the metal/chitosan/antigen complex.

38. The method of claim 37 further comprising resuspending the resulting pellet.

39. An immunogen prepared by the process of:
a) preparing a chitosan solution;
b) chelating a metal ion to the chitosan to produce a metal/chitosan complex, wherein the concentration of metal ion ranges from about 0.7 mM to about 143 mM and wherein the metal ion is selected from the group consisting of zinc and transition metals; and
c) combining an antigen with the metal/chitosan complex.

40. The immunogen prepared by the process according to claim 39, wherein the metal ion is zinc.

41. The immunogen prepared by the process according to claim 39, wherein the transition metal is selected from the group consisting of copper, nickel, and iron.

42. The immunogen prepared by the process according to claim 39, wherein the antigen comprises a protein.

43. The immunogen prepared by the process according to claim 42, wherein the protein comprises a recombinant protein.

44. The immunogen prepared by the process according to claim 43, wherein the recombinant protein further comprises a poly-histidine amino acid sequence.

45. The immunogen prepared by the process according to claim 44, wherein the poly-histidine amino acid sequence is linked to the carboxyl terminus of the protein.

46. The immunogen prepared by the process according to claim 44, wherein the poly-histidine amino acid sequence is linked to the amino terminus of the protein.

47. The immunogen prepared by the process according to claim 44, wherein the protein is attached to the adjuvant through interaction of the poly-histidine amino acid sequence and the metal ion.

48. The immunogen prepared by the process according to claim 39, wherein the chitosan solution is a 1% chitosan solution.

49. The immunogen prepared by the process according to claim 48, wherein the 1% chitosan solution is prepared using a solvent selected from the group consisting of acetic acid and sodium acetate.

50. The immunogen prepared by the process according to claim 39, wherein step b) further comprises sonication of the metal/chitosan complex.

51. The immunogen prepared by the process according to claim 50, wherein step b) further comprises centrifugation of the metal/chitosan complex to form a pellet comprising the metal/chitosan complex.

52. The immunogen prepared by the process according to claim 51 further comprising resuspending the resulting pellet.

53. An immunogen prepared by the process of:
a) preparing a chitosan solution;
b) combining an antigen with the chitosan to form an antigen/chitosan complex; and
c) chelating a metal ion to the antigen/chitosan complex, wherein the concentration of metal ion ranges from about 0.7 mM to about 143 mM and wherein the metal ion is selected from the group consisting of zinc and transition metals.

54. The immunogen prepared by the process according to claim 53, wherein the metal ion is zinc.

55. The immunogen prepared by the process according to claim 53, wherein the transition metal is selected from the group consisting of copper, nickel, and iron.

56. The immunogen prepared by the process according to claim 53, wherein the antigen comprises a protein.

57. The immunogen prepared by the process according to claim 56, wherein the protein comprises a recombinant protein.

58. The immunogen prepared by the process according to claim 57, wherein the recombinant protein further comprises a poly-histidine amino acid sequence.

59. The immunogen prepared by the process according to claim 58, wherein the poly-histidine amino acid sequence is linked to the carboxyl terminus of the protein.

60. The immunogen prepared by the process according to claim 58, wherein the poly-histidine amino acid sequence is linked to the amino terminus of the protein.

61. The immunogen prepared by the process according to claim 58, wherein the protein is attached to the metal/chitosan complex through interaction of the polyhistidine amino acid sequence and the metal ion.

62. The immunogen prepared by the process according to claim 53, wherein the chitosan solution is a 1% chitosan solution.

63. The immunogen prepared by the process according to claim 62, wherein the 1% chitosan solution is prepared using a solvent selected from the group consisting of acetic acid and sodium acetate.

64. The immunogen prepared by the process according to claim 53, wherein step b) further comprises sonication of the antigen/chitosan complex.

65. The immunogen prepared by the process according to claim 53, wherein step c) further comprises centrifugation of the metal/chitosan/antigen complex to form a pellet comprising the metal/chitosan/antigen complex.

66. The immunogen prepared by the process according to claim 65 further comprising resuspending the resulting pellet.

* * * * *